(12) United States Patent
Salven et al.

(10) Patent No.: US 6,936,166 B1
(45) Date of Patent: Aug. 30, 2005

(54) ENDPIECE FOR A CHROMATOGRAPHY COLUMN

(75) Inventors: Owe Salven, Uppsala (SE); Klaus Gebauer, Uppsala (SE); Peter Bellqvist, Uppsala (SE); John Davis, Uppsala (SE); Ulf Pichl, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 58 days.

(21) Appl. No.: 10/482,711

(22) PCT Filed: Jul. 1, 2002

(86) PCT No.: PCT/GB02/02999

§ 371 (c)(1),
(2), (4) Date: Dec. 30, 2003

(87) PCT Pub. No.: WO03/005018

PCT Pub. Date: Jan. 16, 2003

(30) Foreign Application Priority Data

Jul. 4, 2001 (GB) .................................... 0116345

(51) Int. Cl.[7] .............................................. B01D 15/08
(52) U.S. Cl. .................. 210/198.2; 210/232; 210/456; 210/656
(58) Field of Search ............................ 210/198.2, 450, 210/456, 232, 238, 282, 656; 96/101, 105

(56) References Cited

U.S. PATENT DOCUMENTS

| 2,143,248 | A | * | 1/1939 | Otto ......................... 210/532.2 |
| 5,089,125 | A | * | 2/1992 | Hart et al. ................ 210/198.2 |
| 5,137,628 | A | * | 8/1992 | Hart et al. ................ 210/198.2 |
| 5,167,810 | A | | 12/1992 | Vassarotti et al. |
| 5,260,539 | A | * | 11/1993 | Reinke ......................... 219/56 |
| 5,423,982 | A | * | 6/1995 | Jungbauer et al. ........ 210/198.2 |
| 6,576,124 | B2 | * | 6/2003 | Pichl et al. ............... 210/198.2 |
| 6,787,046 | B2 | * | 9/2004 | De Kock et al. ........... 210/748 |
| 2002/0125181 | A1 | * | 9/2002 | Pichl et al. ............... 210/198.2 |
| 2003/0209500 | A1 | * | 11/2003 | Kock et al. .................. 210/748 |

FOREIGN PATENT DOCUMENTS

| SE | 459 396 | 7/1989 |
| WO | WO96/26436 | 8/1996 |

* cited by examiner

Primary Examiner—Ernest G. Therkorn
(74) Attorney, Agent, or Firm—Royal N. Ronning, Jr.; Yonggang Ji; Stephen G. Ryan (57) ABSTRACT

A liquid transfer system (100) comprising a net (170) and a net support (160), wherein, the net (170) is integrally joined with the net support (160). The net (170) and the net support (160) are preferably joined by welding, such as contact welding or by welding at a lower edge (400) of a number of welding-holes (350) that extends through the net support (160).

10 Claims, 7 Drawing Sheets

ENDPIECE FOR A CHROMATOGRAPHY COLUMN

CROSS REFERENCE TO RELATED APPLICATIONS

This application is a filing under 35 U.S.C. § 371 and claims priority to international patent application number PCT/GB02/02999 filed Jul. 1, 2002, published on Jan. 16, 2003 as WO03/005018, and to foreign application number 0116345.0 filed in Great Britain on Jul. 4, 2001, the entire disclosures of which are hereby incorporated by reference.

FIELD OF THE INVENTION

The present invention relates to chromatography columns. More specifically, the invention relates to a net for large-scale chromatography columns.

BACKGROUND OF THE INVENTION

Chromatography columns often contain a net to prevent media from escaping from the end cells which are used for radially distributing the fluid flowing in from a central inlet at one end of the column and for radially collecting the fluid for subsequent outputting from a central outlet at the opposite end of the column. These nets extend across substantially the whole internal diameter of the column. In the prior art the nets have been made of polymer materials and have been attached (with a supporting backing plate if required) to the central inlet resp. central outlet by means of screws or bolts. The screws or bolts are mounted with their heads on the side of the net facing away from the inlet, resp. outlet, and they pass through suitably sized holes in the net and are screwed into suitably threaded axial holes in the wall of the central inlet resp. outlet.

Alternatively nets have been attached by being mounted on a central inlet or outlet tubular port provided with an internal thread and a stop flange positioned on the outside of the port at a distance from the end where the net is to be mounted which is less than the thickness of the net. The net is then positioned against the flange with the end of the port extending into a central opening in the net. The net is held in place by a threaded end piece which has a tubular portion provided with a thread adapted to mate with the thread on the inside of the port, and a flange at one end which pushes the net against the flange on the port when the end piece is screwed up into the port.

One problem with existing arrangements is that it is difficult to give the net proper support, due to the flexible nature of the net. As a consequence, the net may bend if the flow of sample media through the cell is high. In fact, it is common that the net bends to such an extent that it gets plastically deformed, which is highly undesirable as it influences the characteristics of the bed and thus the flow characteristics for the sample. Therefore, the net limits the flow for such columns.

Another problem is that the heads of the mounting screws, resp. the end pieces, project into the bed media and interfere with the packing of the bed media. This may also lead to undesirable fluid-flow characteristics at the top/bottom of the bed.

The heads may also cause dead volumes, i.e. spaces where fluid circulation is slow or non-existent, where particles can collect and this makes cleaning difficult and can lead to sanitary problems.

As used herein and in the appended claims: The term "fluid system" is intended to designate the apparatus in which liquid is either introduced to or withdrawn from a cell at a zone approximately transverse the direction of flow through the cell. The term "cell" is intended to include the terms "vessel" and "column", as well as any other structure utilised by practitioners of the separation arts, to effect a separation and/or extraction of components from an admixture by bringing the admixture into contact with solid or liquid exchange media, above referred to as the packing. "Cross-sectional zone" (or region) refers to a region within a cell bounded by cross sections of the cell-oriented transverse (typically approximately normal) the longitudinal direction of flow through the cell. "Longitudinal direction of flow" refers to the direction of flow from an inlet towards an outlet within a cell. "Longitudinal" is used consistently to designate the dominant flow path of fluid through a cell without regard to direction. "Flow connection system" refers to a system of channels or paths that connect two points in a fluid circuit. While the skilled person realises that columns may be arranged in many different orientations, for the sake of convenience and clarity of description, it will be assumed that the upper end of the column is the inlet end while the bottom end is the outlet end. "Distribution system" refers to structure through which fluids are introduced to a cell and "collection system" refers to structure used to withdraw fluids from a cell, in each instance from a cross-sectional zone.

SUMMARY OF THE INVENTION

The object of the invention is to provide a new way to support the net in a large scale fluid system, which overcomes the drawbacks of the prior art systems. This is achieved by the liquid transfer system as defined in claim 1.

One advantage with such a liquid transfer system is that the net is better supported, whereby plastic deformation of the net may be avoided, and the system may be used at increased flow rates.

Another advantage is that the proposed liquid transfer system is that no parts of the system interfere with the bed.

Still a further advantage is that the proposed liquid transfer system reduces the risk for sanitary problems, due to the simple design comprising few interconnected elements.

Still a further advantage is that the proposed liquid transfer system simple and therefore cheap to produce.

Embodiments of the invention are defined in the dependent claims.

DETAILED DESCRIPTION OF THE INVENTION

Figure 1:
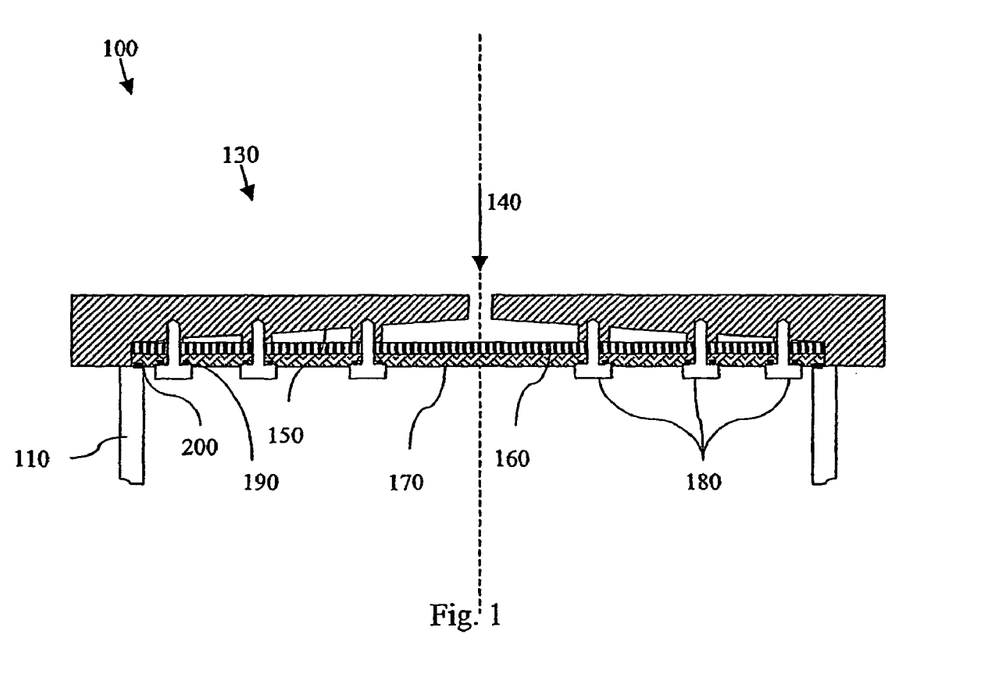
FIG. 1 shows schematically a conventional separator system in cross-section.

FIG. 1 shows schematically a conventional separator system 100 in cross-section. As both ends of such a system often are substantially identical and therefore often either end can be used as the inlet end while the other end is used as the outlet end, only one end is shown. The separator system 100 is essentially rotationally symmetric and it comprises sidewalls 110, and a distribution system 130. The distribution system 130 comprises an inlet 140, and a distribution arrangement 150, for example radially extending ribs, for evenly distributing the mobile phase over the cross-section of the column 100 at the inlet end, and a similar arrangement at the outlet end (not shown) for evenly collecting the mobile phase at the outlet end from the cross-section of the column. The distribution system 130 is terminated by a net support 160, which for instance may be a perforated plate. To prevent the packing from entering the distribution system 130, and to further enhance the distribution, a fine net 170 (mesh) or an equivalent filter material is arranged below the net support 160 facing the packing. As been described above, the net 170 and the net support 160 are attached to the distribution system 130 by screws 180, and in that they are clamped around their outer circumferences between the sidewalls 110 and the distribution system 130. To reduce leakage, sealing means such as O-rings 190, 200 are provided at each screw 180 and around the perimeter of the system respectively.

As mentioned above this arrangement suffers from sanitary problems, e.g. matter collecting in dead volumes, and the screws may cause undesirable fluid-flow characteristics in the bed. Furthermore, in order to achieve acceptable fixation of the net 170 a large number of screws 180 is needed, especially for large diameter columns.

Figure 2:
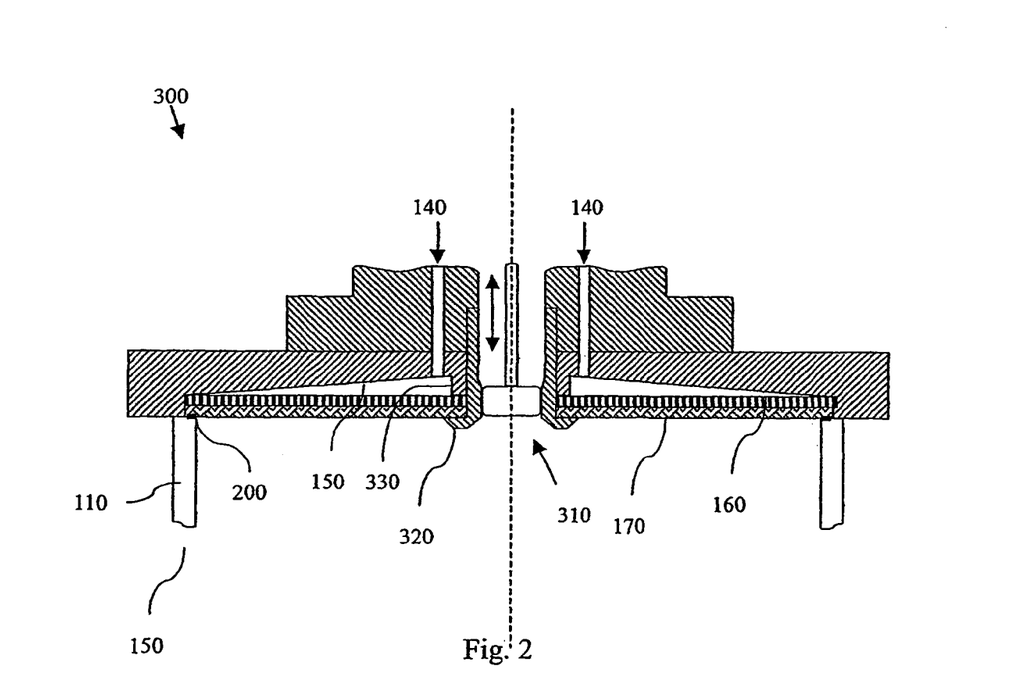
FIG. 2 shows schematically a second prior art separator system.

FIG. 2 shows schematically another prior art separator system 300. This system differs from the system above in that it comprises a central nozzle 310 that can be used to inject slurry or cleaning fluid into the column. The net support 160 and the net 170 therefore each has a central hole with a diameter that is slightly larger than the outer diameter of the central nozzle 310. The central nozzle 310 is further used to centrally fixate the net support 160 and the net 170 by a flange 320 on the outer perimeter of the central nozzle 310, and a second flange 330 on the portion of the central nozzle that extends into the bed. Due to this a lesser number of screws 180 is needed, depending on the size of the system, but the problem relating to screws interfering with the bed still remain.

The present invention avoids these problems by integrally joining the net 170 with the net support 160, such that the net is rigidly fixed to the net support 160, creating an integrated net arrangement. By forming the net support 160 of a material, which is compatible with the material of the net 170, they may for example be joined together by welding.

Figure 3A:
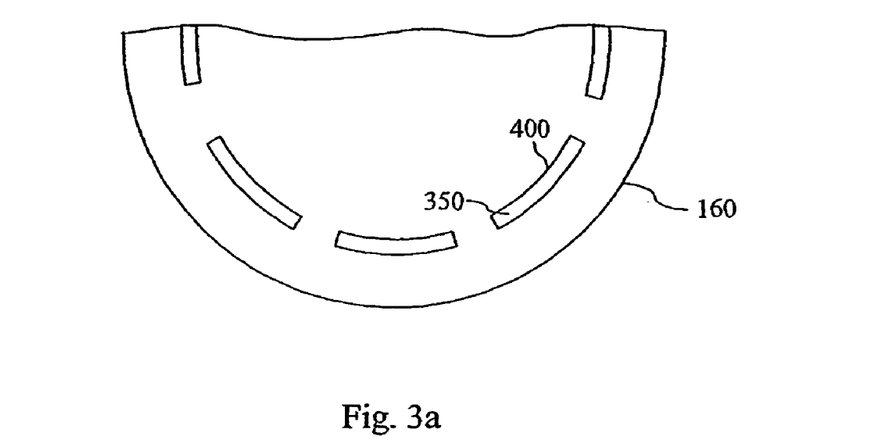
FIGS. 3a–3c show arrangements for fixation of the net to the net support according to the invention.
Figure 3B:
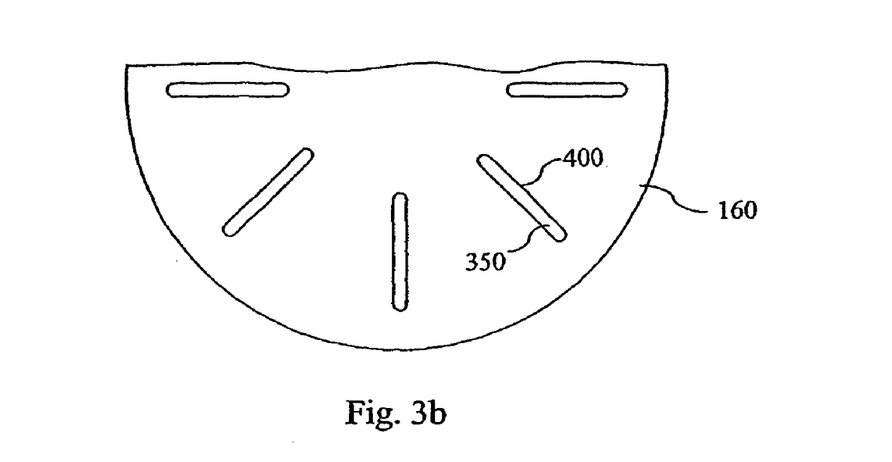
Figure 3C:
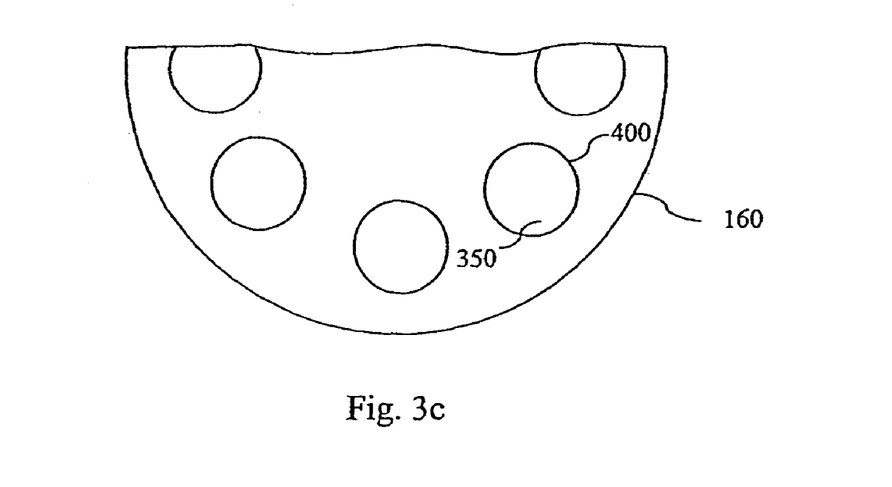
Figure 4:
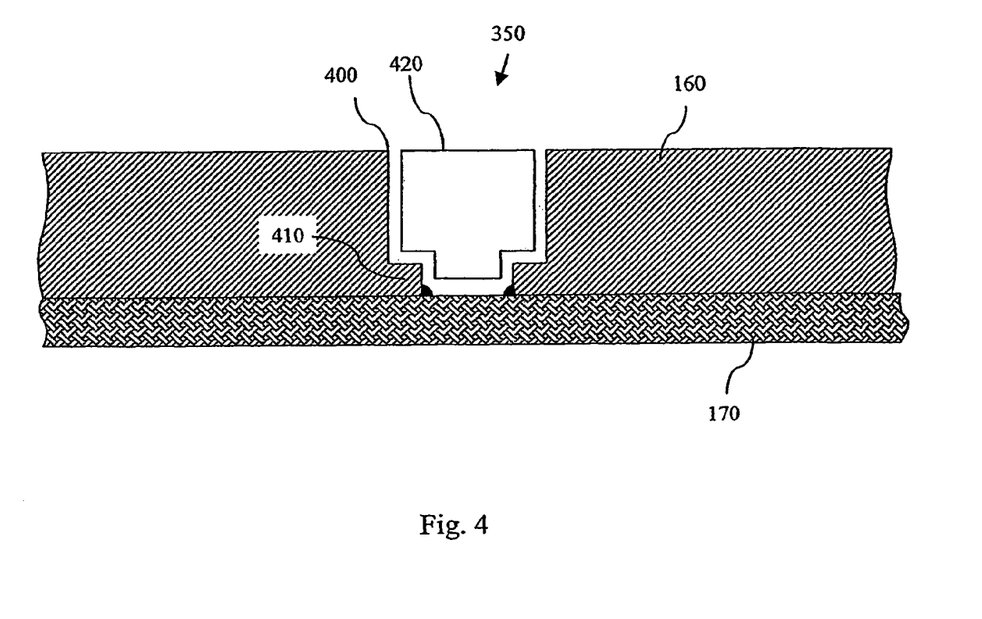
FIG. 4 shows another arrangement for fixation of the net to the net support according to the invention.

There are a number of possible ways to weld the net 170 to the net support 160 e.g. contact welding, continuos or partial welding along a lower edge 400 of a number of welding-holes 350 in the net support 160, together with welding along the outer perimeter of the net. FIGS. 3a–3c show examples of arrangements of welding-holes 350 providing a sufficient fixation of the net. In FIG. 3a the welding holes are arranged as slots along a circle that is concentric with the net support 160. In FIG. 3b the welding holes are arranged as radially extending slots, and in FIG. 3c the slots of FIG. 3a are substituted by circular holes. If the welding-hole arrangement is made such that the holes cover a sufficiently large percent of the area of the system, no extra fluid passages are needed, i.e. the over all perforation of the net support 160 is omitted. To achieve an optimal welded joint or seam, the lower edge 400 of the welding-holes 350 whereto the net 170 is to be welded, may be provided with a small welding-protrusion 410 as is shown in FIG. 4. The welding-protrusion 410 extends in the plane of the net support 160 towards the middle of the welding hole 350, and acts as a material source in the welding process whereby unwanted recesses may be avoided at the edge 400.

One aspect that has to be addressed when designing the net support 160 is that excess volume due to wide holes or other hollow structures should be avoided. The net support 160 should further be adapted to the flow characteristics of the system. However, it may be necessary to make the holes in which the net is to be welded relatively wide as it is difficult to reach down and weld if the hole is to narrow. If the net support 160 has a thickness of about 8 mm a suitable width may be in the magnitude of 20 mm. The welding-protrusion 410 further facilitates the welding as the upper part of the welding holes is given a larger diameter. To reduce the excess volume in the welding holes 350 and to match the flow characteristics, a flow-plug 420 or the like may be provided in the hole. The flow-plug 420 is conveniently made of a machinable or mouldable material, e.g. plastic, and is designed such that the flow path through the welding-hole 350 is divided into one or more smaller paths, that match the flow characteristics of the system. Preferably, the flow-plug 420 is a structure that is centred in the welding hole 350, such that smaller paths are created between the sides of the flow-plug 420 and the walls of the welding hole 350.

Figure 5:
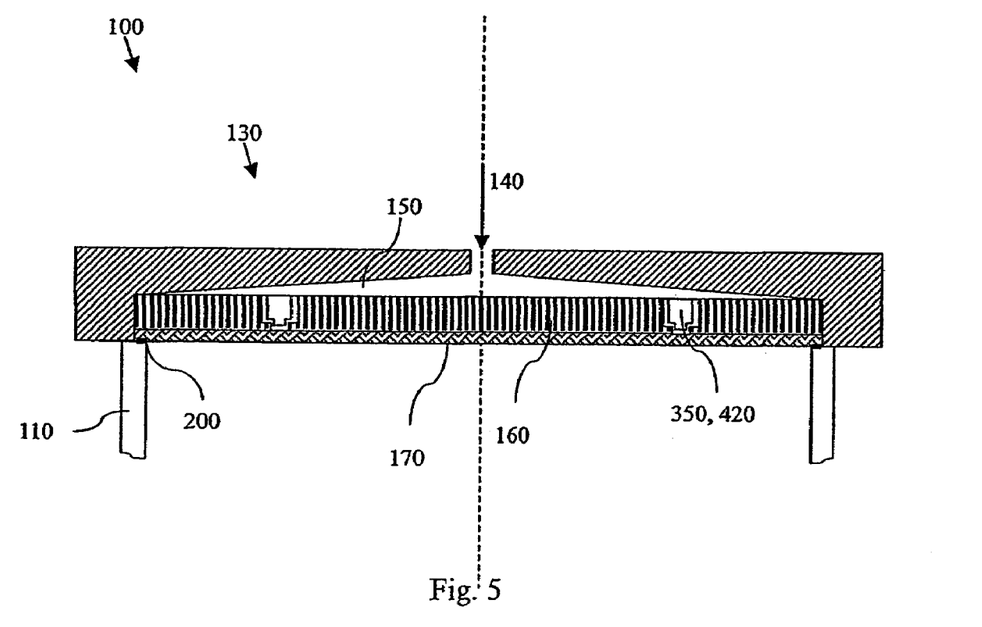
FIG. 5 shows a first embodiment of the present invention.

According to a first embodiment, which is shown in FIG. 5, the net support 160 is formed such that it is rigid enough to be supported only at its outer perimeter. By this all supporting screws and the like may be omitted, whereby interference with the bed is reduced to a minimum. There are several ways in which such a rigid net support 160 may be obtained, such as choosing a more rigid material or increasing the thickness of the material it is made from. As large scale systems may have a column diameter of 400 millimeters up to 2 meters or more, the thickness of the net support 160 have to be appropriate selected for each column diameter. If, for example, a stainless steel plate is used as the net support 160 for a 500 mm column, a thickness of about 3 mm would be useful at normal flow rates, but for a 1.5 m column the thickness of the steel-plate should be 8 to 10 mm. According to this example, a relationship between the column diameter and the thickness of a stainless steel net support 160 is about 500:3. However, it should be noted that the rigidity is further highly dependent on the design of the welding-hole 350 arrangement. Further, if the system is used at higher flow rates, the thickness may have to be increased.

Figure 6:
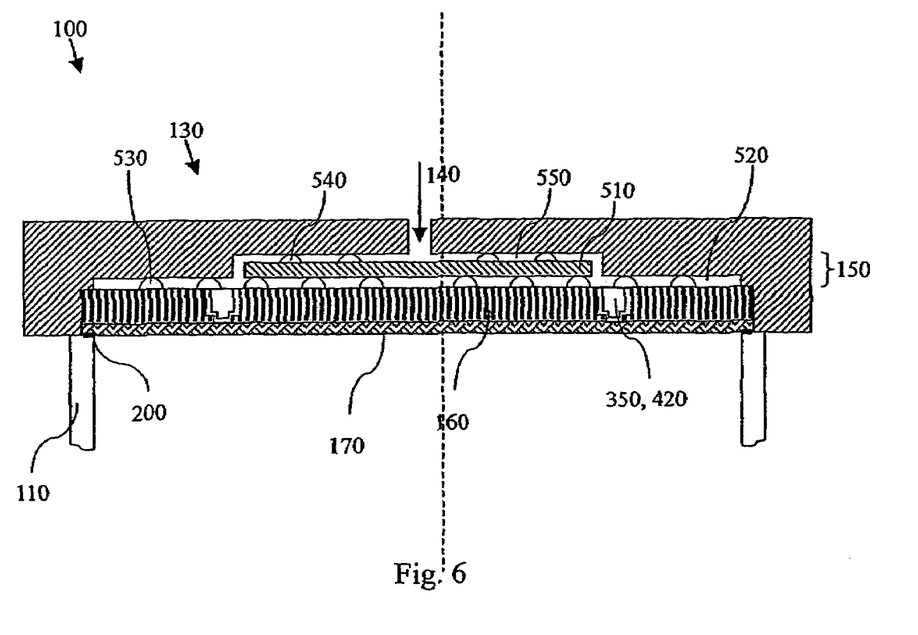
FIG. 6 shows an alternative embodiment of the present invention.

Such a rigid net support 160 may also be formed such that it supports the distribution arrangement 150, such as shown in FIG. 6. In this embodiment the distribution arrangement 150 is comprised of a disc shaped distribution element 510 and a distribution gap 520 that is terminated by the net support 160. A number of spacing elements 530 are provided in between the net support 160 and the distribution arrangement 150, which elements 530 support the distribution element 510 and defines the height of the distribution gap 520. Similar spacing elements 540 are provided in between the distribution element 510 and a main body of the distribution arrangement 150, thereby defining a distribution channel 550. The spacing elements 530, 540 may be provided separate from, or may be integrally formed on the surface on the comprised parts.

Figure 7:
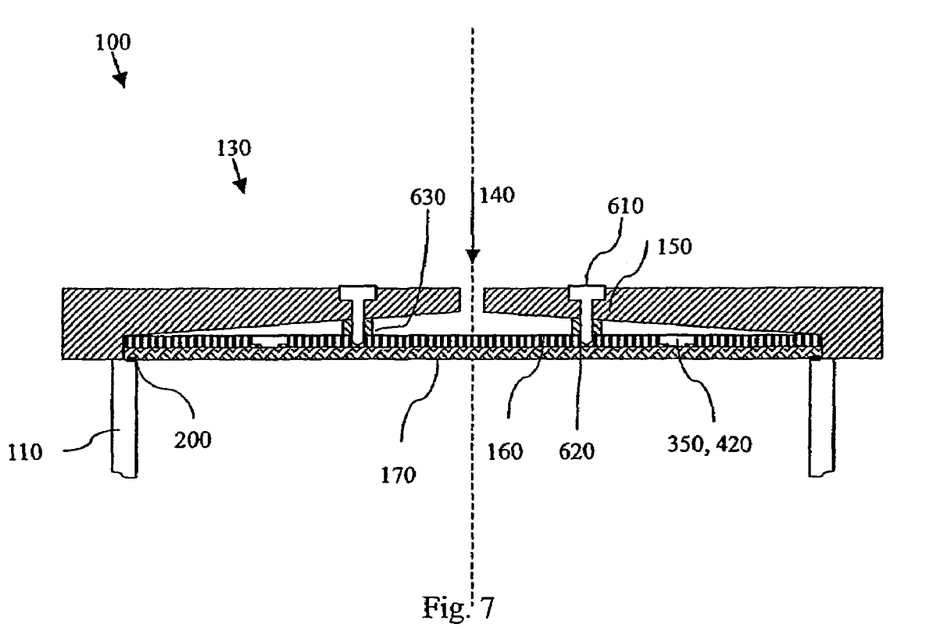
FIG. 7 shows another alternative embodiment of the present invention.

According to another embodiment, which is shown in FIG. 7, the net support 160 is supported at its outer perimeter together with a number of support screws 610 that are evenly spaced to additionally support the net support 160. However, in this embodiment no screws 610 are in direct contact with the bed, as the net support 160 is provided with threaded structures 620 and the screws 610 extends through holes in the distribution system to engage the threaded structures 620. Further, due to that the net 170 is welded to the net support 160, a relatively small number of screws are needed to achieve full support of the net 170. The threaded structures 620 may e.g. be threaded holes in the net support 160 or threaded structures that protrude from the upper surface of the net support 160. Sleeves 630 are provided to set the right distance between the distribution arrangement 150 and the net support 160. If the sleeves 630 are made of a material having sealing properties, e.g. a suitable plastic material, additionally sealing means may be omitted, thus achieving improved sanitary properties.

Either one of the above embodiments may further be adapted for use together with a central nozzle 310, whereby additional rigidity is achieved. In one special embodiment of this type, the central nozzle 310 is integrally joined with the net 170 and the net support 160, whereby many sanitary problems and other problems of prior art are solved.

It should be noted that the present invention is also applicable to columns with non-circular cross-sections, e.g. square or rectangle cross sections, and therefore the term "ring" is not intended to be limited to circular means for retaining a net but is also intended to include means for retaining a net having other shapes e.g. square, rectangular etc.

The present invention is not limited to use with metal nets and metal means for retaining a net welded together but is also applicable to plastic nets and plastic means for retaining a net that may also be welded together. While the invention has been illustrated by the use of welding to join the net and means for supporting the net together it is also conceivable to use any other inherently leak-proof means of joining the net and means for retaining a net such as soldering, brazing, gluing or the like, although welding is the preferred method as it does not introduce any impurities or unwanted substances into the column. It is also conceivable that the nets and means for retaining a net may be formed integrally, for example, by being cast, sintered or moulded in one piece.

What is claimed is:

1. A separation column comprising a net (170) and a net support (160), wherein the net (170) is integrally joined with the net support (160) by welding at the lower edge (400) of a number of welding-holes (350) that extend through the net support (160).

2. The separation column of claim 1, wherein the lower edge (400) is provided with a welding-protrusion (410) that extends in the plane of the net support (160) towards the middle of the welding hole (350).

3. The separation column of claim 1, further comprising a plurality of flow-plugs (420) arranged in the welding-holes (350) to reduce excess volume.

4. The separation column of claim 1, wherein the net support (160) is rigid and supported only at its outer perimeter.

5. The separation column of claim 4, wherein the net support (160) is a stainless steel plate with a ratio between thickness and diameter of between 8:1500 and 10:1500.

6. A separation column of claim 1, wherein the net support (160) is provided with threaded structures (620), whereby the net support (160) is secured to a distribution system (130) by screws (610) that extend through holes in the distribution system (130) and engage said threaded structures (620).

7. A separation column of claim 1, wherein the net support (160) supports a distribution arrangement (150) formed by a disc shaped distribution element (510) and a distribution gap (520).

8. A separation column of claim 7, wherein the distribution arrangement (150) is supported by the net support (160) through a number of spacing elements (530) that are provided in between the net support (160) and the distribution arrangement (150).

9. A separation column of claim 1, further comprising a central nozzle (310) that is integrally joined with the net (170) and the net support (160).

10. The separation column of claim 1, wherein said welding holes (350) do not extend through the net (170).

* * * * *